US005762622A

United States Patent [19]
Lamont

[11] Patent Number: 5,762,622
[45] Date of Patent: Jun. 9, 1998

[54] MEDICAL BOOT WITH UNITARY SPLINT

[76] Inventor: William D. Lamont, 54283 Meadowood Ct., Shelby Township, Maccomb County, Mich. 48316

[21] Appl. No.: 521,962

[22] Filed: Aug. 31, 1995

Related U.S. Application Data

[63] Continuation-in-part of Ser. No. 343,090, Nov. 21, 1994, Pat. No. 5,609,570.

[51] Int. Cl.⁶ .................................................. A61F 5/00
[52] U.S. Cl. ............................ 602/65; 602/27; 602/28
[58] Field of Search .............................. 602/5, 23, 27–29, 602/60, 65; 36/140, 145, 153, 154, 178, 181

[56] References Cited

U.S. PATENT DOCUMENTS

| | | | |
|---|---|---|---|
| 4,478,214 | 10/1984 | Lamont | 128/149 |
| 4,974,583 | 12/1990 | Freitas | 602/27 X |
| 5,020,523 | 6/1991 | Bodine | 602/27 |
| 5,050,620 | 9/1991 | Cooper | 602/27 |
| 5,143,058 | 9/1992 | Luber et al. | 602/28 |
| 5,162,041 | 11/1992 | Simmons | 602/65 |
| 5,224,925 | 7/1993 | Varn | 602/28 |
| 5,226,245 | 7/1993 | Lamont | 36/9 R |
| 5,372,576 | 12/1994 | Hicks | 602/27 |
| 5,429,588 | 7/1995 | Young et al. | 602/27 |
| 5,437,621 | 8/1995 | Andrews et al. | 602/42 |
| 5,460,600 | 10/1995 | Bieling | 602/27 |
| 5,569,174 | 10/1996 | Varn | 602/27 |
| 5,609,570 | 3/1997 | Lamont | 602/65 |

Primary Examiner—Richard J. Apley
Assistant Examiner—Kim M. Lee
Attorney, Agent, or Firm—Charles W. Chandler

[57] ABSTRACT

A medical boot comprising a relatively soft boot component having a foot portion and a leg portion, and a relatively hard plastic splint formed with a foot portion and a leg portion. The foot portion of the splint is mounted inside the boot and the leg portion of the splint is outside the rear surface of the boot. Releasable fastening means connect the splint to the rear surface of the boot.

6 Claims, 6 Drawing Sheets

MEDICAL BOOT WITH UNITARY SPLINT

CROSS-REFERENCE TO RELATED APPLICATIONS

This application is a continuation-in-part of Ser. No. 08/343,090, filed Nov. 21, 1994, now U.S. Pat. No. 5,609,570.

BACKFROUND OF THE INVENTION

This medical boot is an improvement over the boot described in my prior U.S. Pat. No. 4,478,214 issued Oct. 23, 1984, and also U.S. Pat. No. 5,226,245 which was issued Jul. 13, 1993.

The boot disclosed in my U.S. Pat. No. 5,609,570 which issued Mar. 11,1997 is formed with a soft wicking material that reduces any shear force acting on the tissue of the skin. The boot has a substantially seamless construction to avoid the problem of stitched seams impeding capillary flow and creating tissue trauma.

Under some circumstances, my prior boot is relatively large for small limbed patients. A smaller sized boot will readily accommodate relatively small limbed patients such as children and the elderly. My co-pending patent application also discloses a novel plastic splint for use with the larger boot.

A plastic splint useful for some prior art medical boots is disclosed in U.S. Pat. No. 5,224,925, which issued Jul. 6, 1993, to Harold T. Varn.

SUMMARY OF THE INVENTION

The broad purpose of the present invention is to provide an improved medical boot. The preferred embodiment of the boot is formed from a one-piece section of trilaminate material. The interior boot lining is made of a soft wicking material such as nylon type 6, polyester, and a polyurethane foam loop laminate available from Velcro USA, Inc. The boot material is cut, sealed and then the edges at the bottom of the boot joined together in a longitudinal seam with reference lines for exact placement of an exterior ambulatory sole. This is the only stitched seam. All other edges are heat sealed to form stitchless seams that are gentle to the patient's skin tissue.

The boot has a pair of straps for opening and closing the boot. In its closed condition, the boot has a large toe opening that provides ventilation and permits the patient's toes to extend beyond the toe of the boot. A relatively hard plastic insole is disposed in the boot to support a walking patient. A fabric liner covers the top side of the insole to provide a soft material in contact with the patient's foot. The opposite ends of the insole are received in a pair of pockets carried at opposite ends of the insole liner. The forward pocket has a pair of male snaps that mate with female snaps carried in the boot bottom to prevent the hard insole from slipping, and also allowing the fast and simple changing to another clean insole liner or a gel filled polymer insole for greater support of a sensitive diabetic foot when ambulatory.

An exterior sole can also be attached by hook and loop fastener means to the boot bottom to assist the user in ambulating. A laminated hook material on the sole attaches to loop material on the boot body.

A hard plastic unitary splint with a heel portion and a leg portion is received through a heel opening in the boot. The foot portion of the splint has a profile generally accommodating the configuration of the bottom of the boot. The leg portion of the splint extends up and outside the back leg portion of the boot. A molded strip hook fastener on the splint is releasably attached to the outer liner of the boot. The splint can also be easily and quickly removed from the boot.

A brace can be attached to the heel portion of the splint. The brace extends at right angles to the splint to provide lateral support for the patient's foot when he is disposed in a supine position.

A bridge also can be readily connected between two splints. The bridge has its opposite ends connected to a pair of splints to support both of the user's feet in a supine position.

The splint is made of an polypropylene plastic in such a manner that by heating the splint heel, the leg portion of the splint can be bent to a new position with respect to the splint's foot.

The boot can also be used with the cushion disclosed in my prior patents to create a heel well to prevent ulceration of the user's heel, while protecting both sides of the ankle bone.

Still further objects and advantages of the invention will become readily apparent to those skilled in the art to which the invention pertains, upon reference to the following detailed description.

DESCRIPTION OF THE DRAWINGS

The description refers to the accompanying drawings in which like reference characters refer to like parts throughout the several views, and in which.

DESCRIPTION OF THE PREFERRED EMBODIMENT

Figures 1, 2, 3:
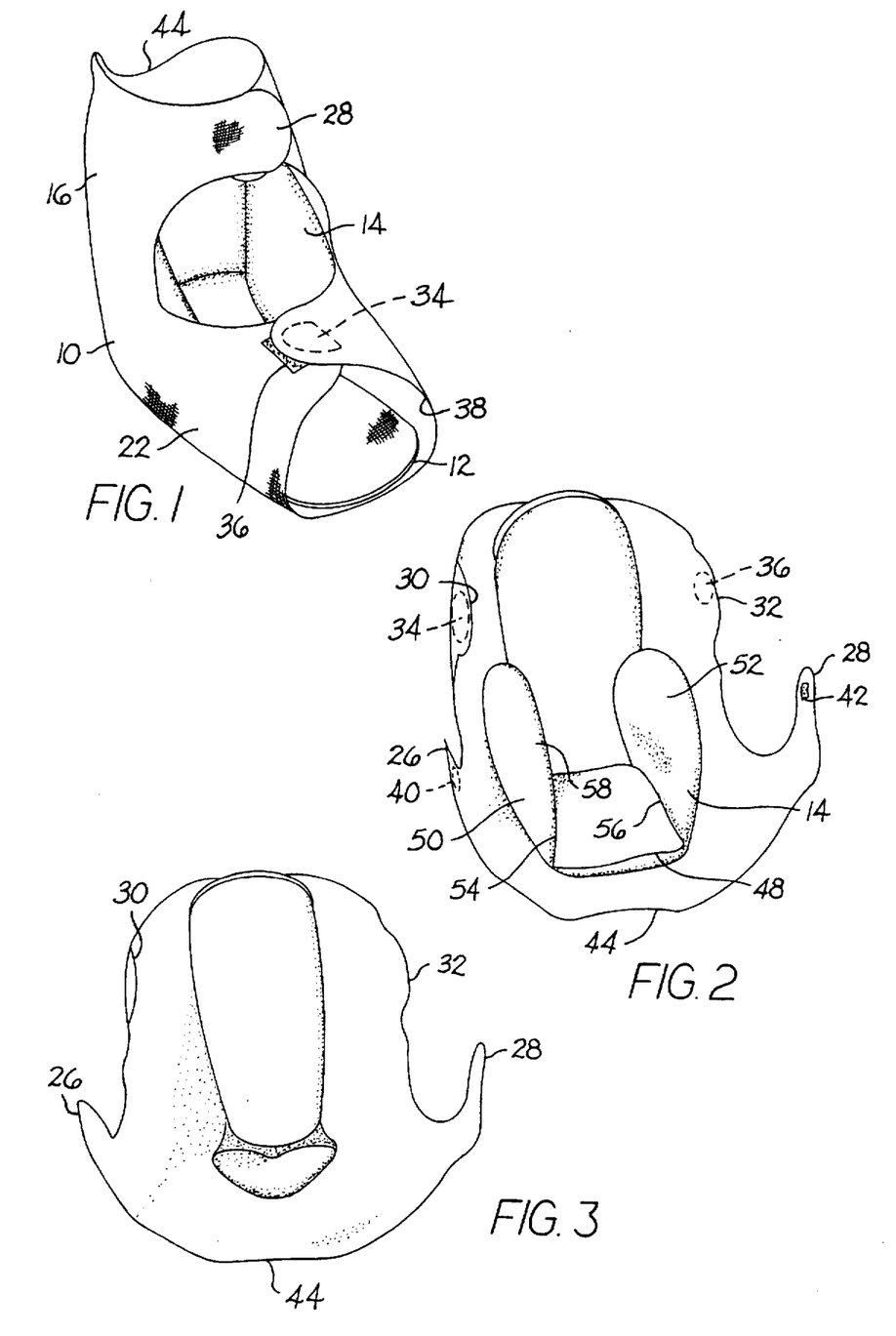
FIG. 1 illustrates the preferred embodiment of the invention disposed in an upright, closed condition.
FIG. 2 illustrates the preferred boot disposed on its back in an open condition showing a gel filled cushion disposed in the boot.
FIG. 3 is a view similar to FIG. 2 but showing the gel filled cushion removed from the boot.

Referring to the drawings, FIG. 1 illustrates a medical boot 10 illustrating a preferred embodiment of the invention. Boot 10 has a height of about 10", and a length from heel to toe of 10". The boot has an internal hard insole, see FIG. 5, enclosed in insole liner 12, and a cushion 14 disposed adjacent the boot's heel to form a heel well.

Figure 4:
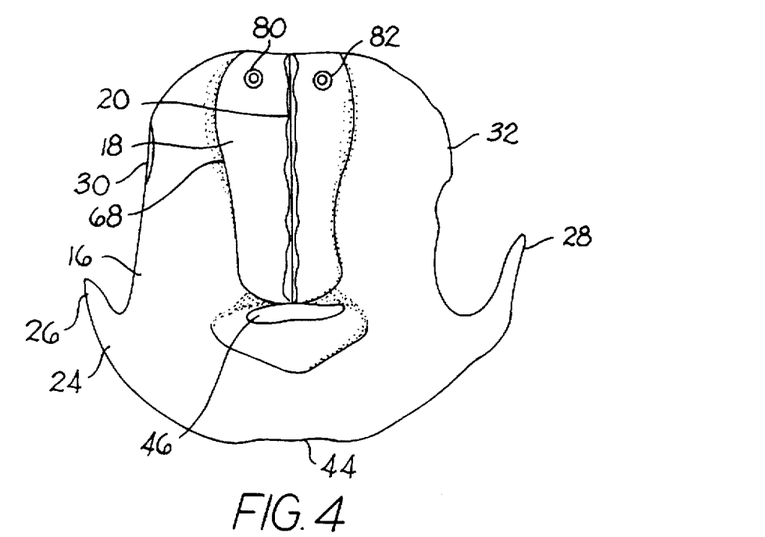
FIG. 4 is similar to FIG. 3 but shows the hard insole removed from the boot.

Referring to FIGS. 1 and 4, the boot has an upper leg portion 16 and a sole 18. The boot is formed from a single multi-layer sheet containing the profile of the leg portion and the sole. The sole is formed from a pair of edges that are stitched together at 20 in a seam extending from the heel to the toe of the boot.

The boot material is made of an elastomeric shape-retaining material, such as a soft, flexible compressible open cell polyurethane foam core, with an outer layer 22 of an ultra smooth, soft, non-allergenic cloth such as brushed tricot. This type of fabric is characterized by a continuous layer of small loops which makes the material compatible with fabric hook fastener means, such as Velcro fasteners. The entire outer cover including both the upper portion of the boot and the sole has a brushed tricot covering so that a patch of a Fastener hook material can be connected in any position on the boot exterior.

The inner boot liner is a laminated self-wicking material 24 such as nylon Type C Polyester and Polyurethane Foam Loop 3973 laminate available from Velcro USA, Inc. Such material has no surface fibers that can get into a patient's wound but has excellent wicking properties because it attracts perspiration accumulating on the user's tissue. The inner liner material is available from Guilford Mills. The material has no fleece, paper, fibers or vinyl requiring corn starch powder. It reduces shear and effectively controls skin moisture.

As in my co-pending patent application, the entire edge of the boot above the sole is heat fused and compressed together and cut to the boot configuration all in one process.

The boot has a pair of cooperating leg straps 26 and 28, and a pair of cooperating foot straps 30 and 32. Foot strap 30 has a patch 34 of a fabric hook material which may be connected to a complementary patch 36 of a fabric loop material (FIG. 1) on strap 32 to close the boot around the patient's foot. Note that in the closed position illustrated in FIG. 1, the boot has a large toe opening 38. Similarly, leg strap 26 has a patch of a Velcro hook fastener material 40 on its outer side which mates with a patch 42 of a fabric loop material to close the boot such that the boot encircles the user's leg as illustrated in FIG. 1.

The top rear of the boot has a recessed area at 44 which extends about 1½" down from the top of the boot and is about 3½" wide to protect the rear of the user's leg against skin irritation, and to prevent constriction of capillary flow in the lower calf area of the leg.

Referring to FIG. 4, the boot heel has an opening 46 that is 2¾" wide from side to side and about 1¼" tall, which receives the splint and provides greater air circulation to the heel area.

Cushion 14 is illustrated in FIGS. 1 and 2 and is similar to the configuration illustrated in my co-pending application. The cushion has a central portion 48 and a pair of side panels or wings 50 and 52. The cushion has the same material construction as the remainder of the boot, that is with an inner core of a flexible, compressible, polyurethane foam with an outside covering of a brushed tricot material. The central portion 48 of the cushion has a somewhat rectangular configuration while the side panels 50 and 52 fold along the side edges of the central panel and extend at about a 45° angle from a pair of parallel fold lines 54 and 56.

The central portion and side panels of the cushion each have an internal recess, not shown, housing a fluid-tight plastic container filled with an air, water, and gel combination. It is identical to the cushion illustrated in my co-pending patent application.

The cushion is mounted in the boot with the rectangular central body portion adjacent the back of the boot with the side panels disposed adjacent the boot sides. The particular positions of the side panels are adjusted to accommodate the size of the user's foot to form a well beneath the user's heel. When located in position, a patch of a Velcro fastener on the bottom side of the central portion as illustrated in FIG. 2, engages the internal boot liner.

Figure 5:
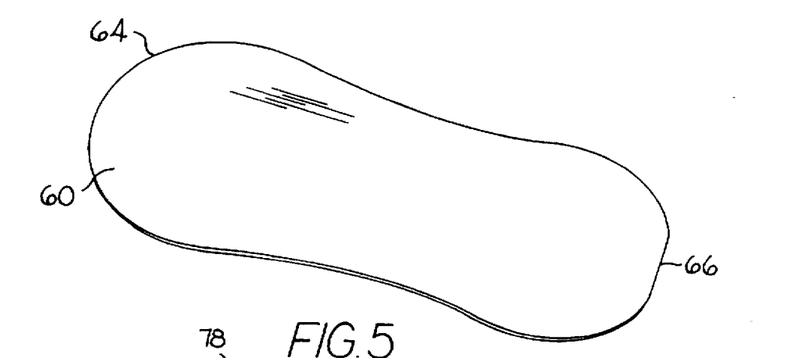
FIG. 5 illustrates the hard insole.
Figure 6:
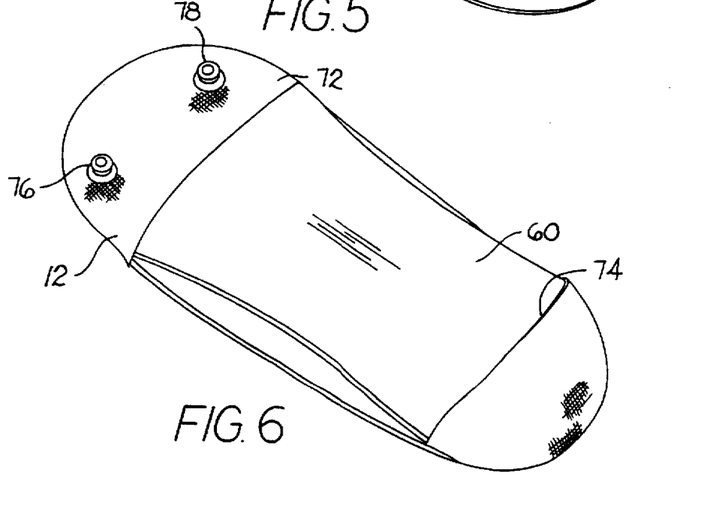
FIG. 6 illustrates the hard insole disposed in the insole liner.

A hard insole 60, illustrated in FIG. 5, is inserted in liner 12 as illustrated in FIG. 6. FIG. 6 shows the liner and the insole in the upside down position. Insole 60 is elongated with a toe end 64 and a heel end 66. The insole has a configuration which generally corresponds to a heat formed recessed line or crease 68 illustrated in FIG. 4 and formed in the bottom of the boot. The hard insole is available in various lengths, such as small, medium and large for a typical boot. The hard insole and liner 12 extend beyond the toe opening of the boot so that the patient's toes are well ventilated.

Insole liner 12 has a top surface formed with a soft foam interior and a brushed tricot surface to provide a soft surface for the patient's foot. The bottom side of the liner has a pair of pockets 72 and 74 for receiving the heel and toe of insole 60. The hard insole is formed of an ABS plastic material so that it is relatively stiff and rigid but can be bent longitudinally as well as laterally. It provides some foundation support for the patient when he is either walking with the boot or confined to bed.

Pocket 72 has a pair of male snap fasteners 76 and 78 which mate with a pair of female fasteners 80 and 82 mounted in the bottom of the boot body. The female snap fasteners have a bottom button component recessed in the material of the bottom sole. The snap fasteners locate the hard insole in position and prevent it from slipping in the boot as the patient is either walking or lying in a supine position.

Figure 7:
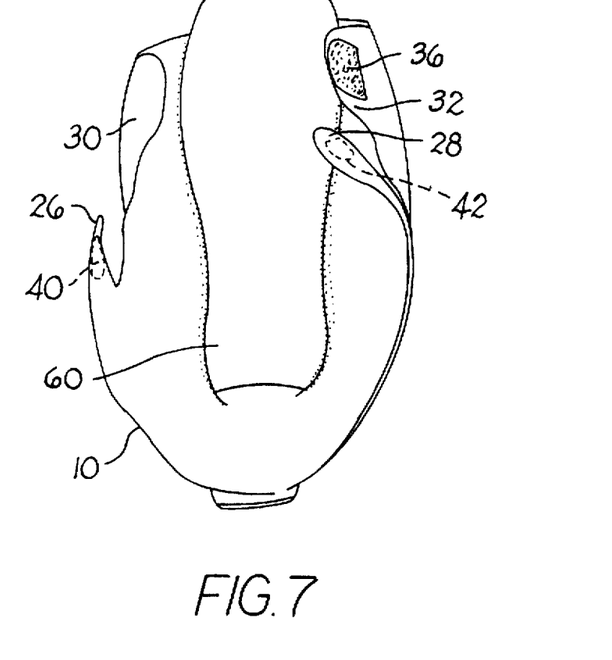
FIG. 7 is a view showing the boot supported by the splint.
Figure 10:
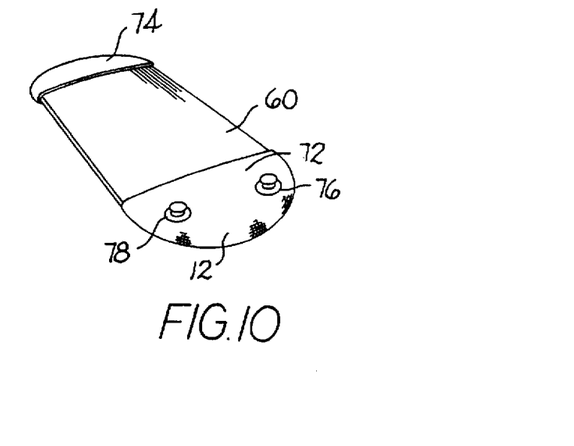
FIG. 10 shows the bottom of the hard insole liner.

FIG. 7 shows the hard insole in its liner mounted in the bottom of the boot. The inside liner is also illustrated in FIG. 10.

Figure 9:
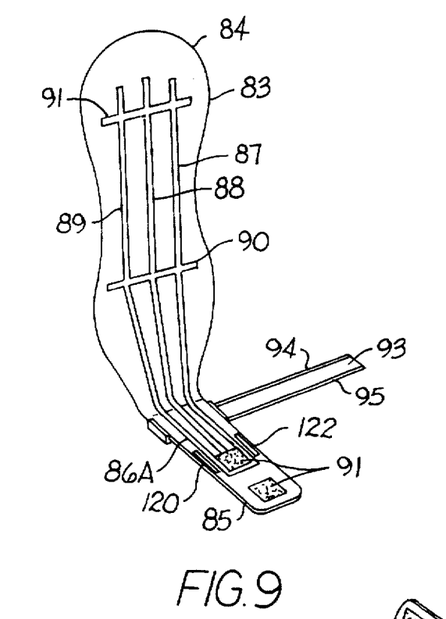
FIG. 9 shows a splint connected to a lateral brace.
Figure 11:
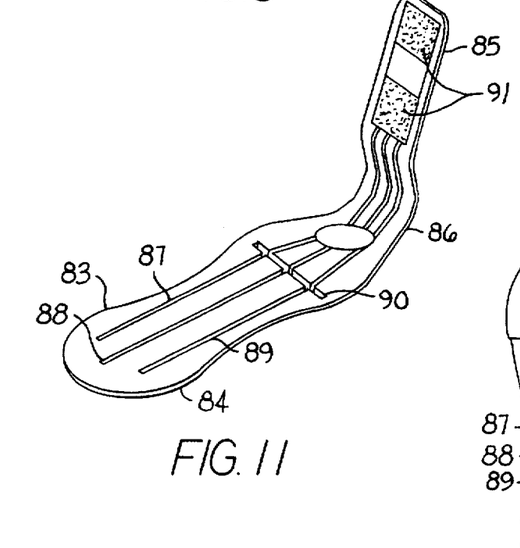
FIG. 11 shows the splint removed from the boot.
Figure 12:
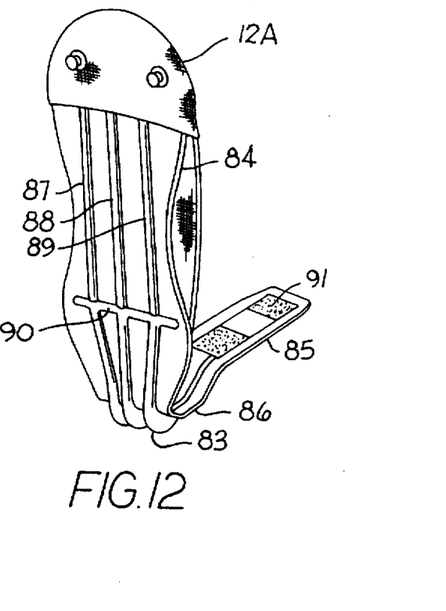
FIG. 12 is another view showing the splint mounted in the insole liner.

A unitary splint 83 is illustrated in FIGS. 9, 11, and 12. Splint 83 has a relatively flat construction with a foot-support sole section 84 and a leg-support section 85. The splint is about ⅛" thick; the splint sole is 11" long and the splint leg-support section has a height of about 7½". The sole has a width of about 3¾" and has a somewhat hour-glass shape resembling that of insole 60. Heel 86 joins the sole and the leg section of the splint. Heel 86 has a concave reinforced configuration. The heel has a planer section 86A about 1.96 inches wide.

Both the heel, sole and the leg sections of the splint have three spaced longitudinally extending ribs, 87, 88 and 89 which are parallel to one another, and cross ribs 90 and 91. The ribs are all raised on the bottom of the splint so that there are no protuberances irritating the patient's foot.

Figure 8:
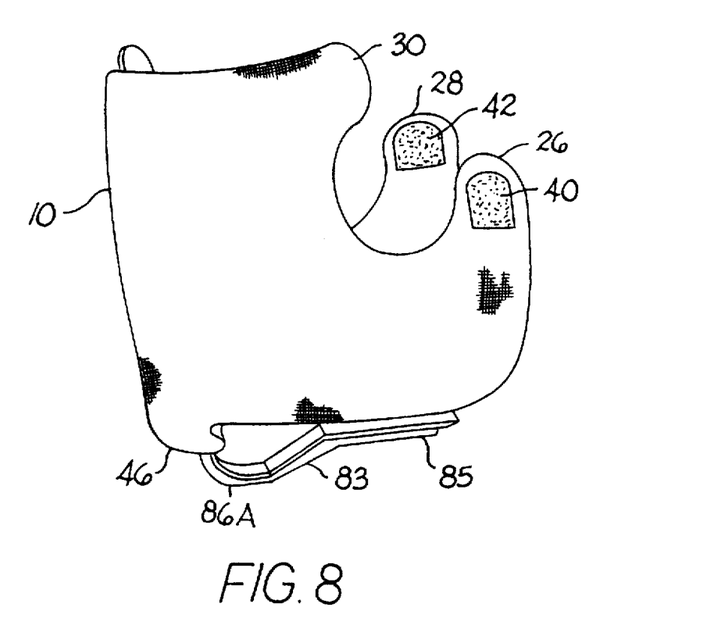
FIG. 8 is a view similar to FIG. 7 but showing the side of the boot.

The width of the splint back is about 2" wide, and is such that the back portion can be passed through opening 46 of the boot to the position illustrated in FIG. 8 in 5 which the splint sole is on the inside against the bottom of the boot and leg section 85 is adjacent the rear outer covering of the boot body. The leg-support section of the splint has a fabric hook patch means 91 molded into the plastic which readily attaches to the outer covering of the boot in an adjusted location. Thus, the sole of the splint is located by its position inside and adjacent the sole of the boot while the splint leg is connected to 10 the rear of the boot by hook fastener patch means 91. The splint sole is relatively rigid with a slight bendability.

The splint provides the advantages of a multi-component splint, but a one-piece element which can be easily slipped into or removed from the boot to support the patient's foot, preventing foot drop and ankle contractions when the patient is disposed in a supine position. As shown in FIG. 12, the splint can be partially encased in a fabric liner 12A similar to liner 12 shown in FIG. 6. Thus, the splint foot-support sole section 84 is generally interchangeable with insole member 60 as regards the splint disposition in the boot.

Figure 13:
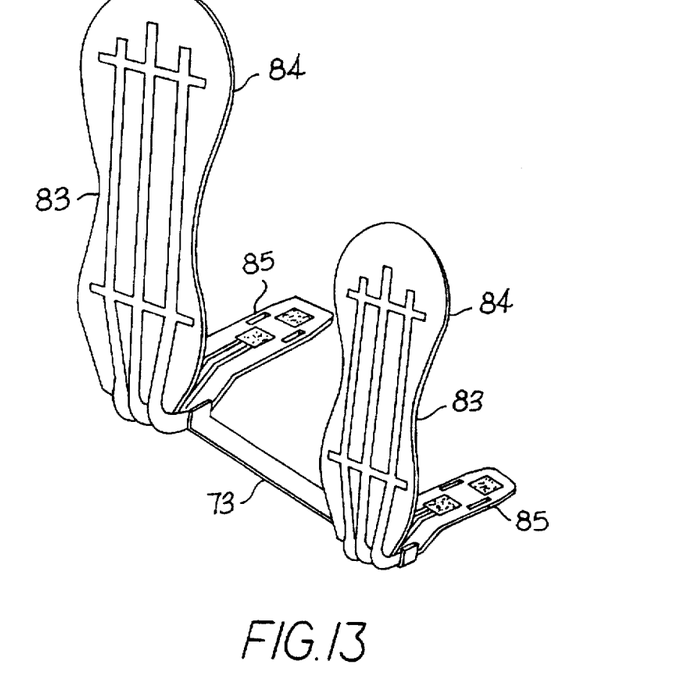
FIG. 13 shows a bridge connected to two splints.
Figure 16:
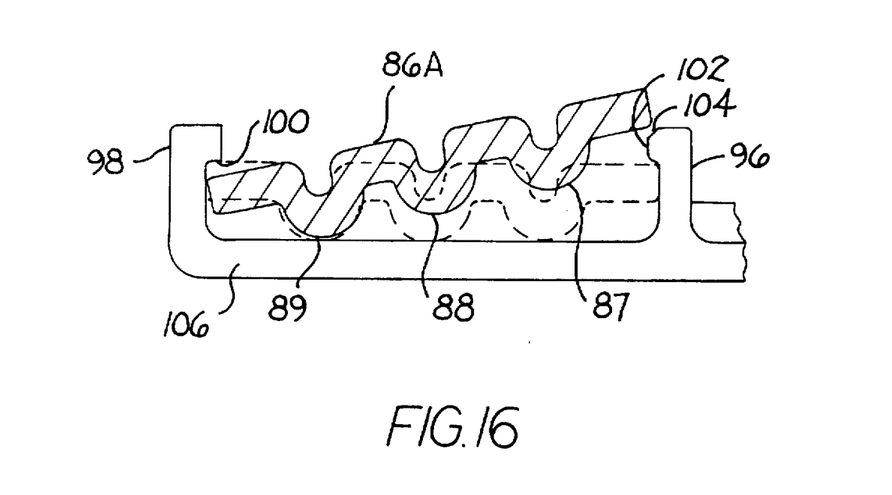
FIG. 16 is an enlarged view showing the manner in which the heel of splint is inserted into the channel locking section of the lateral brace.

A lateral brace 93, illustrated in FIG. 9 is also formed of polypropylene plastic material about 7½" long, 0.90" wide and ⅛" thick with a pair of longitudinal stiffening ribs 94 and 95. Referring to FIGS. 16 and 17 bar 93 has a pair of short parallel walls 96 and 98 having their inner sides spaced a distance of about 1.975" apart, that is, slightly greater than the width of the heel section 86A of the splint. Two walls 96 and 98 are slightly resilient and the outer ends of the two walls have a pair of inwardly directed lips 100 and 102 respectively. Lip 102 has an outwardly disposed slightly chamfered edge 104 for receiving the splint heel section 86A in such a manner that by inserting one side edge of the splint inside the channel formed by the two walls and beneath lip 100, the other side edge of the splint heel sections 86A can be disposed on the chamfered section 104 and pass downwardly so as to bend heel sections 86A 96 outwardly until the splint leg has passed beneath lip 102. The height of the lips above the base 106 of the channel is such that the splint sections 86A is snugly trapped as a snap-fit within the channel. This arrangement provides a tight fitting splint connection in which the brace is disposed at 90° with respect to the splint. Brace 93 provides lateral support preventing the user's foot from tilting toward the side in which the brace is disposed. The brace can be attached to the splint so as to extend in either direction from the splint, i.e. to the right or to the left in FIG. 9. FIG. 13 shows two similarly-constructed splints 83 joined together by an elongated bridge 73. The bride has snap-connection channel walls at each of its ends, whereby the bridge can be releasably attached to two splints arranged in side-by-side relation. Each set of channel walls can be similar to the channel walls 96 and 98 shown in FIG. 16. Bridge 73 combines the stabilizing function of two braces, of the type depicted in FIG. 9. The bridge can be considered as the equivalent of two separate braces.

Figure 14:
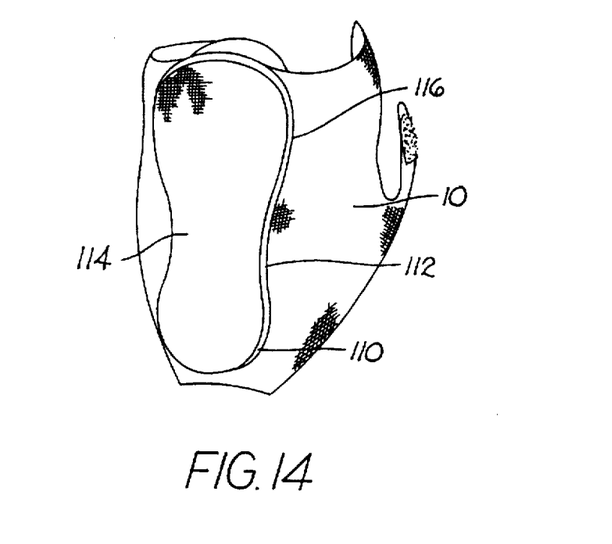
FIG. 14 is a view showing the exterior walking sole attached to the bottom of the boot.
Figure 15:
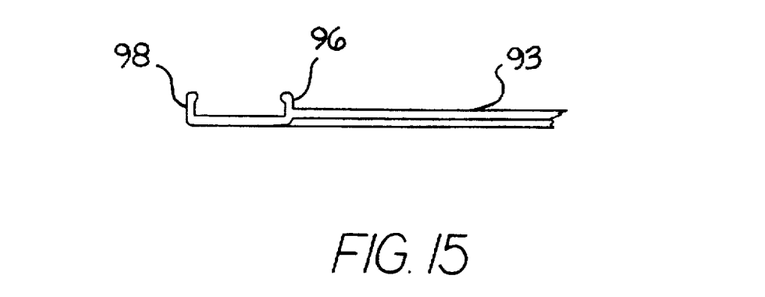
FIG. 15 illustrates a side view of a lateral brace.

FIG. 14 illustrates a relatively substantial trilaminate external sole 110 mounted on the bottom of boot 10. Sole 110 has a thickness of ½", a length of 9⅛" and a maximum width of about 4". Sole 110 has a cushioned mid-section 112, and a bottom layer about 1/16" thick with a formed ground-engaging bottom surface 114. The opposite side of sole 110 has a continuous layer of a hook-shaped fabric type fastener material 116 which can be readily attached to the Velcro fastener compatible outer liner of the boot. Sole 110 can be readily attached to the boot when the user wants to walk, or be removed from the boot when the patient is lying down.

As shown in FIG. 9, the leg portion of the splint has a pair of parallel slots 120 and 122 for receiving an external strap (not shown) which secures the boot body to the splint. The slots are parallel to the length of the leg portion and about ⅛" wide and 2¼" long and parallel to one another.

Thus, it is to be understood that I have described an improved boot that is somewhat smaller than my prior boots to accommodate patients having relatively small legs and feet. The boot material is cut from a trilaminate material offering a smooth interior, eliminating shear against the skin. The outer liner is a hook-compatible material that enables the patient provider to engage the straps on the front of the boot at various locations to secure the foot and the leg into the boot. The bottom sole permits the patient to ambulate without any straps, belts or other fasteners. The soft wicking material on the interior of the boot wicks away moisture. The boot can be used with an internal cushion to suspend the user's heel when the patient is lying in a supine position. The cushion can be horizontally adjusted to adjust the size of the heel well.

The hard insole of the boot is contained in a liner that can be easily removed for cleaning without interrupting patient treatment by merely unsnapping the liner and sliding it with the insole out through the toe opening. Interchangeability of the various sizes of the hard insole makes the boot simple and cost effective and reduces the inventory required of the medical institution.

Having described my invention, I claim:

1. A medical boot comprising: a boot-shaped body formed of a trilaminate material that includes a resilient plastic foam core layer, a first layer formed of a soft wicking material, and a second surface layer formed of a soft non-allergenic cloth, said first surface layer constituting the inner surface of the boot, said second surface layer constituting the outer surface of the boot;

a heat-formed narrow recess indented in the inner surface of the boot body in a pattern having a plan configuration of a person's foot, whereby said recess circumscribes a sole for the boot body;

a relatively hard stiff insole member formed separately from said boot body, said insole member having an edge configuration of substantially the same shape as said sole;

whereby said insole member can be placed within the boot body against said sole, with its edge seated in said narrow recess;

releasable fastener means on said insole member and sole for releasably attaching said insole member to the sole of said boot body;

said boot body having a foot-encircling portion adapted to encircle the foot, a leg-encircling portion adapted to encircle the leg, a toe opening adapted to receive the toes, and a heel opening adapted to receive the heel;

a rigid unitary splint formed separately from said boot body, said splint having a foot-support section, a leg support section, and a heel section;

said splint being installable on the boot body so that the foot-support section of the splint is located within the boot body in facial engagement with said sole, and the leg-encircling portion of the boot body; and means for releasably attaching the leg-support section of the splint to the leg-encircling portion of the boot body.

2. The medical boot of claim 1, wherein the foot-support section of the splint has an edge configuration that is similar to the edge configuration of said insole member, whereby said foot-support section and said insole member are interchangeable in the boot body.

3. The medical boot of claim 1, wherein said foot-support section of the splint has a fabric liner thereon and a snap fastener element on said liner engageable with the aforementioned fastener means on the sole of said boot for releasably attaching the splint to said boot sole; said foot-support section of the splint having a toe end; said fabric liner having a pocket fitting around the toe end of said foot-support section.

4. The medical boot of claim 1, and further comprising an elongated rigid brace adapted to have a snap-fit connection on the heel section of the splint; said brace being oriented at right angle to the heel section of the splint, to provide lateral support for the boot when the patient is disposed in a supine position.

5. The medical boot of claim 1, and further comprising an elongated rigid brace having a longitudinal dimension, said elongated brace having two transverse upstanding walls (96, 98); said upstanding walls having facing lips (100, 102) spaced from said brace to form a transverse channel; the heel section of said splint having side edges adapted to slightly spread said upstanding walls to permit said heel section to have a snap-fit in the transverse channel, whereby said brace is connected at a right angle to the splint.

6. The medical boot of claim 5, wherein said brace has similarly-constructed transverse walls at each end of the brace, whereby said brace can be used as a bridge between two similarly-constructed splints.

* * * * *